(12) United States Patent  (10) Patent No.: US 7,495,433 B2
Daalmans et al.  (45) Date of Patent: Feb. 24, 2009

(54) DEVICE FOR DETECTING DEFECTS IN ELECTRICALLY CONDUCTIVE MATERIALS IN A NONDESTRUCTIVE MANNER

(75) Inventors: Gabriel Daalmans, Höchstadt (DE); Martin Steck, Steinheim (DE)

(73) Assignee: Siemens Aktiengesellschaft, Munich (DE)

( * ) Notice: Subject to any disclaimer, the term of this patent is extended or adjusted under 35 U.S.C. 154(b) by 207 days.

(21) Appl. No.: 10/592,295

(22) PCT Filed: Feb. 23, 2005

(86) PCT No.: PCT/EP2005/001888

§ 371 (c)(1),
(2), (4) Date: Sep. 8, 2006

(87) PCT Pub. No.: WO2005/085832

PCT Pub. Date: Sep. 15, 2005

(65) Prior Publication Data

US 2007/0200563 A1 Aug. 30, 2007

(30) Foreign Application Priority Data

Mar. 8, 2004 (EP) .................................. 04005462

(51) Int. Cl.
*G01N 27/83* (2006.01)
*G01R 33/12* (2006.01)
(52) U.S. Cl. ........................................ 324/238; 324/235
(58) Field of Classification Search ................ 324/217, 324/219, 220, 222, 223, 228, 234–243
See application file for complete search history.

(56) References Cited

U.S. PATENT DOCUMENTS

| 4,303,883 | A | * | 12/1981 | Mori et al. ............. 324/207.18 |
| 4,594,549 | A | * | 6/1986 | Smith et al. .................. 324/232 |
| 4,924,293 | A |   | 5/1990 | Saito et al. |
| 5,243,547 | A |   | 9/1993 | Tsai et al. |
| 5,491,409 | A | * | 2/1996 | Flora et al. .................. 324/242 |
| 5,842,986 | A |   | 12/1998 | Avrin et al. |
| 6,031,273 | A |   | 2/2000 | Torok et al. |
| 6,329,818 | B1 | * | 12/2001 | Tokunaga et al. ........... 324/252 |
| 6,452,384 | B1 |   | 9/2002 | Becker et al. |

(Continued)

FOREIGN PATENT DOCUMENTS

DE  43 18 716 A1  12/1994
DE  199 45 944 A1  5/2001

OTHER PUBLICATIONS

NVE Corporation, "Introduction to NVE GMR Sensors", Online, Nov. 15, 2002, URL:http://www.megatron.fr/composants/pdf/pdfgmr/Senosr_Catalog_111402-Introduction_to_GMR_Sensors1. pdf>, Retrieved on May 24, 2005,XP002329240, pp. 1-8.

(Continued)

*Primary Examiner*—Kenneth J Whittington

(57) ABSTRACT

Disclosed is a device for detecting defects which are deep in electrically conductive materials in a non-destructive manner, comprising an excitation device provided with induction coils which are used to produce low frequency eddy currents in the material, and a receiving device for the magnetic field of the eddy currents, the magnetic field being modified by the defects, and the receiving device comprising a gradiometer magnetic field sensors with an integrated bridge circuit.

10 Claims, 4 Drawing Sheets

U.S. PATENT DOCUMENTS 6,504,363 B1 * 1/2003 Dogaru et al. ............... 324/235
6,911,826 B2 * 6/2005 Plotnikov et al. ........... 324/529
2002/0060565 A1 5/2002 Tondra

OTHER PUBLICATIONS

R.S. Indeck, J.H. Judy and S. Iwasaki, "A Magnetoresistive Gradiometer", IEEE Transactions on Magnetics, IEEE, Inc., New York, US, vol. 24, No. 6, Nov. 1, 1998, pp. 2617-2619, XP 000031789.

C.P.O. Treutler, "Magnetic Sensors for Automotive Applications", Sensors and Actuators A, Elsevier Sequoia, S.A., Lausanne, CH., vol. 91, No. 1-2, Jun. 5, 2001, pp. 2-6, XP004239165.

* cited by examiner

DEVICE FOR DETECTING DEFECTS IN ELECTRICALLY CONDUCTIVE MATERIALS IN A NONDESTRUCTIVE MANNER

CROSS REFERENCE TO RELATED APPLICATIONS

This application is the US National Stage of International Application No. PCT/EP2005/001888, filed Feb. 23, 2005 and claims the benefit thereof. The International Application claims the benefits of European Patent application No. 04005462.9 filed Mar. 8, 2004. All of the applications are incorporated by reference herein in their entirety.

FIELD OF THE INVENTION

The invention relates to a device for detecting defects which are deep and close to the surface in electrically conductive materials in a nondestructive manner, having an exciter device with induction coils for producing low-frequency eddy currents in the material, and having a reception device for the magnetic fields of the eddy currents, which fields have been changed by the defects.

BACKGROUND OF THE INVENTION

The conventional solution to the problem of detecting deep defects in electrically conductive materials in a nondestructive manner is the use of a low-frequency eddy-current method using induction coils for excitation and detection purposes. This method has a sensitivity which is strongly dependent on the exciter frequency and breaks down properly at low frequencies. An attempt is generally made to compensate for the weakness of the sensor by increasing the exciter current. In the prior art, no particular value has been placed on preventing inductive signals which can easily exceed the magnetic-field signals, in particular at relatively high frequencies (kHz range).

$V_{Det}=V(B)+V(\delta B/\delta t)$, where $V(B)<V(\delta B/\delta t)$ for relatively high frequencies.

The inductive signals are very inconvenient for two reasons. Firstly, additional lift-off signals may result which are perceived as defect signals, and secondly it is no longer possible for quantitative material testing to be carried out in a nondestructive manner since the amplitude and phase of the detector voltage have been distorted.

SUMMARY OF THE INVENTION

The invention is therefore based on the object of developing a device of the type mentioned at the outset such that it can advantageously be used over a relatively wide frequency range and therefore, firstly, can detect deep, hidden faults and surface faults and, secondly, a quantitative relationship is made possible between the detector signal and the defect size and depth and such that, finally, the quality of the sensor can be fully utilized even in an environment with electromagnetic interference.

In order to achieve this object, the invention provides for the reception device to contain gradiometer magnetic-field sensors with an integrated bridge circuit, in one development of the invention the integrated bridge circuit preferably having a folded loop area.

Although the use of gradiometer magnetic-field sensors, for which purpose magnetoresistive transducers of any desired design can be used, results in a smaller signal than in the case of the previously used induction coils, there is a better signal-to-noise ratio. Owing to the integrated bridge circuit, in the case of which virtually one half of the bridge is folded into the other such that virtually no notable loop area still remains in which voltages could be induced, owing to the change in magnetic fields, which distort this measurement result, the device according to the invention becomes, to a high degree, independent of external interference fields, with the result that, in addition to very low frequencies, relatively high frequencies can also be used.

In order to obtain information, by means of an eddy-current method, from the deep material regions, i.e. from depths of greater than 1 mm, it is necessary to produce very strong eddy-current fields at the depth of the component, which is physically impeded by the skin effect, however. Low frequencies penetrate very deep into the material, but have, purely physically, a poor spatial resolution, and therefore the fault size which can be detected is limited. Higher frequencies have a better spatial resolution but, as the frequency increases, the measurement sensitivity is restricted to an ever greater extent by electromagnetic interference effects.

Owing to the device according to the invention it is now possible to increase the measurement sensitivity by electromagnetic interference effects largely being minimized and it therefore being possible to work in deep material regions, i.e. at depths of approximately 10 mm, even at higher frequencies.

Owing to the extension of the inventive approach as has already been mentioned above, in accordance with which approach the integrated bridge circuit also has a folded loop area, an arrangement is achieved in which the very small loop area remaining which may be available for the induction of interference voltages is split into two parts which have flows in opposite directions, with the result that such induced voltages are largely cancelled.

In accordance with one further feature of the present invention, the bridge circuit of the magnetic-field sensors, whose basic length should not be greater than the maximum test depth, can be arranged on a compact chip which, for its part, can in turn preferably be arranged on a board, which is provided with a connection plug, of an eddy-current measuring head, it being possible for the chip feed lines to be shielded by a metalized underside of the board, with little induction. Owing to this measure, the possible interference potential is also switched off in the region of the feed lines since it is not on its own sufficient for interference voltages to be avoided on the actual measuring part, i.e. the integrated bridge circuit comprising the gradiometer magnetic-field sensors, but ultimately interference occurring in the feed lines would distort the result in the same way.

The chip board according to the invention can in this case be used in various low-frequency measuring heads, to be precise first of all such that the chip board protrudes into a circumferential induction coil producing the exciter field and, in the process, protrudes forwards from this induction coil, slightly in the direction of the workpiece to be investigated. Secondly, the induction coils can also be arranged on a yoke, between whose limbs the chip board protrudes such that the exciter field runs essentially at right angles to the chip. This variant is particularly suitable for testing at a very high resolution since in this case there is no magnetic-field component of the exciter field in a direction parallel to the chip area, with the result that the chip virtually does not see the exciter field at all and cannot be directly influenced by it.

BRIEF DESCRIPTION OF THE DRAWINGS

Further advantages, features and details of the invention are given in the description below relating to some exemplary embodiments and with reference to the drawing, in which.

DETAILED DESCRIPTION OF THE INVENTION

Figure 1:
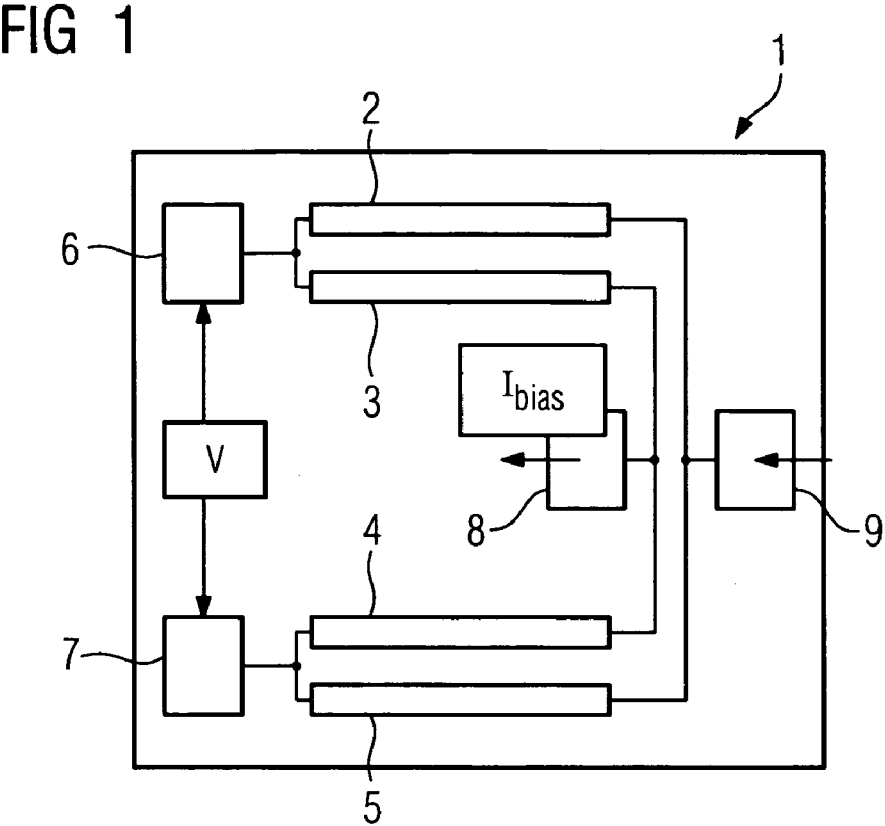
FIG. 1 shows a view of a chip having an integrated bridge circuit arranged thereon comprising gradiometer magnetic-field sensors.

FIG. 1 shows a chip 1, on which an integrated bridge circuit comprising four magnetically sensitive resistors 2 to 5 is arranged, 6 and 7 indicating contact areas for connecting the tap-off lines for the resulting measured voltage V, and 8 and 9 indicating corresponding conductor connections for feeding a supply current $I_{bias}$ into the converter bridge.

The bridge circuit with the chip feed lines (13, 14, 15, 16) is designed to have such a low inductance that the signal output voltage of the bridge circuit is essentially proportional to the magnetic field of the eddy currents and not their induction.

Figure 2:
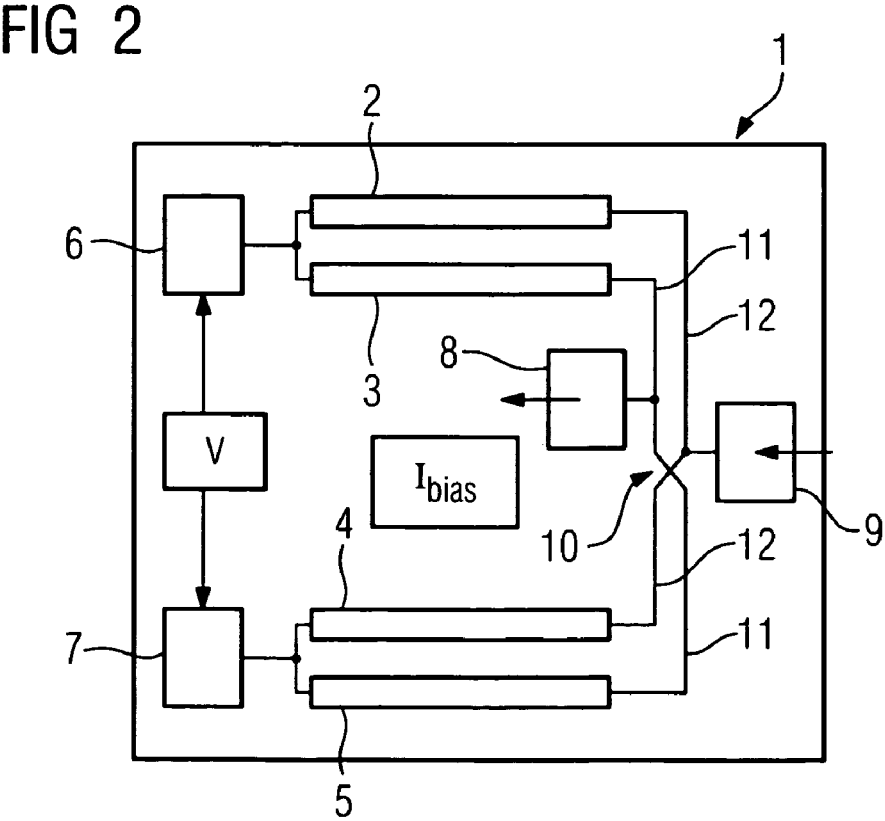
FIG. 2 shows a modified embodiment of the arrangement shown in FIG. 1 with an additionally folded loop area.

In the arrangement shown in FIG. 2, the loop area is also folded (see point of intersection 10 between the connecting lines 11 and 12, which in this case are of course guided one over the other in isolated fashion).

Such a low-induction converter bridge as shown in FIGS. 1 and 2 is integrated in an eddy-current measuring head so as to avoid substantial inductive contributions. For this purpose, the chip 1 (cf. in particular FIG. 3) is mounted on a chip board 13 which has, in addition to the feed lines 14 to 17 on the chip side, an electrically conductive coating 18 on the underside, which ensures that the chip feed lines 14 to 17 for current and voltage have a little induction. A plug is plugged on at the upper end of the board 13 in FIG. 3.

The exciter device for producing the eddy currents is designed and arranged such that, when applied to fault-free material, the exciter device does not produce a signal voltage.

Figure 3:
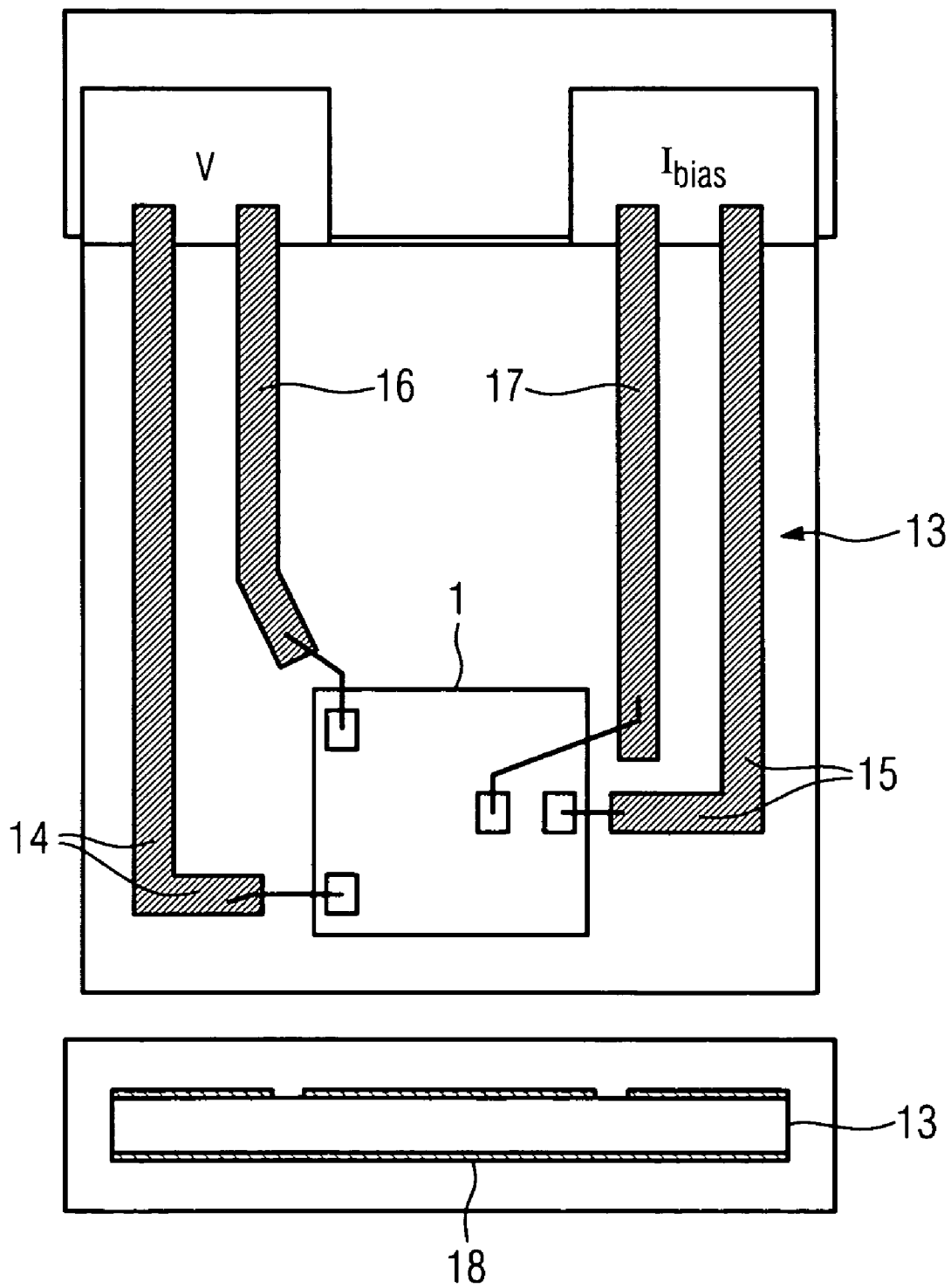
FIG. 3 shows a schematic arrangement of a chip as shown in FIGS. 1 and 2 on a chip board having a connection plug and shielded feed lines, as a plan view and a view from the front.
Figure 4:
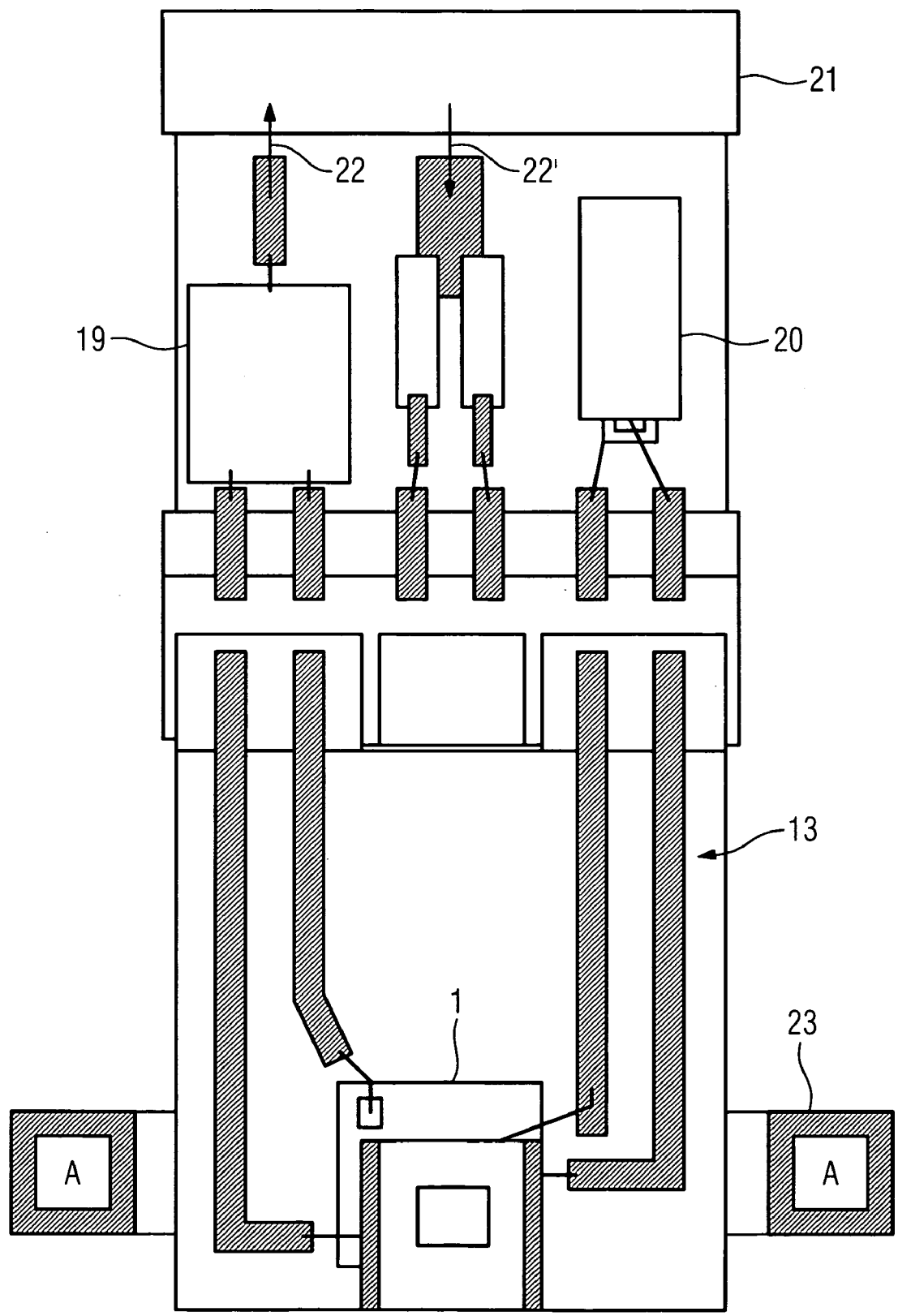
FIG. 4 shows a low-frequency measuring head, two different variants being indicated for the excitation A and B.
Figure 5:
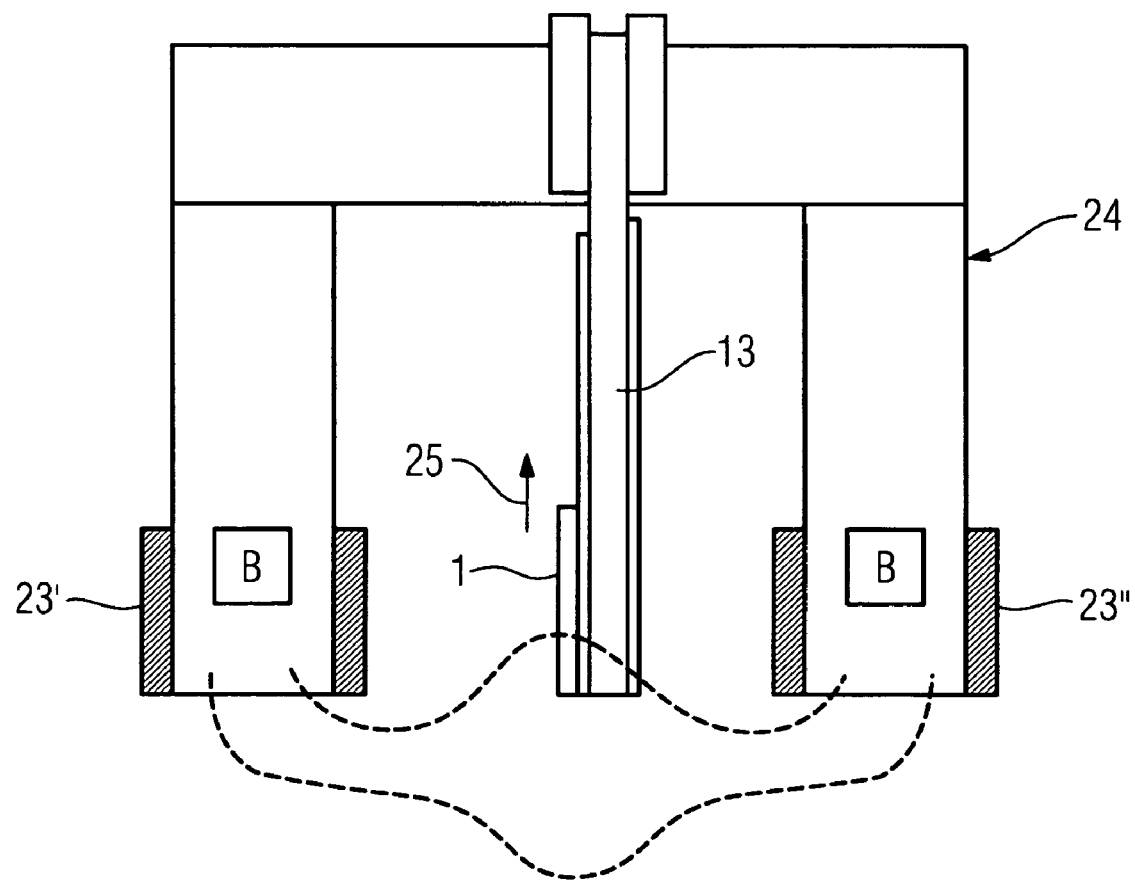
FIG. 5 shows a side view, rotated through 90°, of the arrangement shown in FIG. 4, in the variant B for the excitation of the workpiece using a yoke.

This is the case, for example, in the embodiment as is illustrated in FIG. 4, the board with the chip being identical to the design shown in FIG. 3; part of the drive circuit with a preamplifier 19, a battery 20 and a cable plug 21 to the measuring unit is also illustrated. The arrow 22' indicates the exciter current, while arrow 22 schematically reproduces the signal output voltage.

The variant illustrated at A for exciting the eddy currents in the material under investigation comprises a circumferential coil 23, through which the chip 1, which is arranged on the chip board 13, protrudes forwards, in which case the converter is completely subjected to the exciter field. The refinement of the bridge circuit according to the invention does, however, ensure that the excitation in the bridge does not produce any significant gradient contribution.

Even more suitable and even less susceptible to interference is variant B, in which the induction coils 23' and 23" are arranged on a yoke 24, into which the chip 1, which is arranged on the chip board 13, protrudes such that no magnetic-field component is provided in the direction of the arrow 25 and therefore the chip virtually does not see the exciter field, which is illustrated by dashed lines.

The design according to the invention results in a whole series of advantages. Firstly, the measuring device can be used not only at very low frequencies but also in the frequency range of from 10 Hz to 10 kHz, which makes it possible to examine the fault with resolution in terms of depth. Secondly, the measuring device allows for quantitative analysis of the dimensions of the fault. Thirdly, and finally, the measurement method according to the invention can also be carried out in adverse conditions since external interference fields virtually do not impair the measurement accuracy.

The invention claimed is:

1. A defect detecting device for non-destructively detecting defects in an electrically conductive material, comprising:
    an exciter device that generates a low-frequency signal for detecting defects in the electrically conductive material;
    a yoke having a planner surface where the yoke is essentially U-shaped having a first end of the U-shape and a second end of the U-shape connected by a connecting section of the U-shape;
    first induction coil arranged at the first end of the U-shaped yoke, the first induction coil being connected to the exciter that transmits an electromagnetic signal and induces an eddy current in the material;
    a second induction coil arranged at the second end of the U-shaped yoke, the second induction coil being connected to the exciter that transmits an electromagnetic signal and induces a further eddy current in the material; and
    a reception device connected to the exciter device containing magnetoresistive gradiometer magnetic-field sensors with an integrated-bridge circuit having a plurality of chip feed lines, where the reception device extends from the yoke at essentially right angles to and between the first and second induction coils such that no magnetic field component is provided at the reception device, wherein
    the integrated bridge circuit with chip feed lines is configured to have inductance such that the signal output voltage of the integrated bridge circuit is essentially proportional to the magnetic field of the eddy currents and configured to detect the eddy current induced magnetic fields that indicate defects of the material, and
    the exciter device is designed and arranged such that when the generated electromagnetic signal is applied to fault-free material, the exciter device does not produce a signal output voltage.

2. The device as claimed in claim 1, wherein the integrated bridge circuit has a folded loop area.

3. The device as claimed in claim 2 wherein the length of the bridge circuit of the magnetic-field sensors is not greater than the maximum test depth.

4. The device as claimed in claim 3, wherein the bridge circuit is arranged on a compact chip.

5. The device as claimed in claim 4, wherein the chip is arranged on a chip board having a connection plug of a eddy-current measuring head and the chip feed lines are shielded by a metallized coating of the underside of the chip board.

6. A device for non-destructively detecting defects in an electrically conductive material, comprising:

an exciter device that generates a low-frequency signal for detecting defects in the electrically conductive material;

a yoke having a planner surface where the yoke is essentially U-shaped having a first end of the U-shape and a second end of the U-shape connected by a connecting section of the U-shape;

a first induction coil arranged on the first end of the yoke;

a second induction coil arranged on the second end of the yoke, where the first and second induction coils are connected to the exciter device and transmit a low-frequency signal and induce an eddy current in the material; and a reception device connected to the exciter device arranged on the connecting section of the U-shape yoke essentially equidistant between the first and second ends of the yoke and essentially perpendicular to the planner surface of the yoke such that no magnetic field component is provided to the reception device, the reception device containing a plurality of magnetoresistive gradiometer magnetic-field sensors with an integrated-bridge circuit having a plurality of chip feed lines wherein the integrated bridge circuit with chip feed lines is configured to have inductance such that the signal output voltage of the integrated bridge circuit is essentially proportional to the magnetic field of the eddy currents and configured to detect the eddy current induced magnetic fields that indicate defects of the material, and the exciter device is designed and arranged such that when the generated low-frequency signal is applied to fault-free material, the exciter device does not produce a signal output voltage.

7. The device as claimed in claim 6, wherein the integrated bridge circuit has a folded loop area.

8. The device as claimed in claim 7 wherein the length of the bridge circuit of the magnetic-field sensors is not greater than the maximum test depth.

9. The device as claimed in claim 8, wherein the bridge circuit is arranged on a compact chip.

10. The device as claimed in claim 9, wherein the chip feed lines are shielded by a metallized coating of the underside of the compact chip.

* * * * *